US005162526A

United States Patent [19]

Brois et al.

[11] Patent Number: 5,162,526

[45] Date of Patent: Nov. 10, 1992

[54] MACROCYCLIC POLYAMINE AND POLYCYCLIC POLYAMINE MULTIFUNCTIONAL LUBRICATING OIL

[75] Inventors: Stanley J. Brois, Westfield; Antonio Gutierrez, Mercerville, both of N.J.

[73] Assignee: Exxon Chemical Patents Inc., Linden, N.J.

[21] Appl. No.: 737,302

[22] Filed: Jul. 29, 1991

Related U.S. Application Data

[60] Continuation of Ser. No. 429,177, Oct. 30, 1989, abandoned, which is a division of Ser. No. 902,779, Sep. 2, 1986, Pat. No. 4,880,923, which is a division of Ser. No. 550,977, Nov. 16, 1983, Pat. No. 4,637,886, which is a continuation-in-part of Ser. No. 453,143, Dec. 27, 1982, abandoned, which is a continuation-in-part of Ser. No. 415,980, Sep. 8, 1982, abandoned, which is a division of Ser. No. 243,781, Mar. 16, 1981, abandoned, which is a continuation of Ser. No. 67,546, Aug. 17, 1979, Pat. No. 4,283,857, which is a continuation-in-part of Ser. No. 817,217, Jul. 20, 1977, Pat. No. 4,174,322, and Ser. No. 806,326, Jun. 13, 1977, Pat. No. 4,167,514, which is a division of Ser. No. 726,206, Sep. 24, 1976, Pat. No. 4,062,786.

[51] Int. Cl.[5] .................. C07D 257/02; C07D 255/02; C07D 237/04

[52] U.S. Cl. .................................. 540/474; 544/242; 544/296

[58] Field of Search ................ 544/242, 296; 540/474

[56] References Cited

U.S. PATENT DOCUMENTS

| | | | |
|---|---|---|---|
| 2,658,895 | 11/1953 | Ballard et al. | 544/242 |
| 2,713,559 | 7/1955 | Smith | 544/242 |
| 3,219,666 | 11/1965 | Norman et al. | 544/383 |
| 3,254,025 | 5/1966 | LeSuer et al. | 252/32.7 E |
| 3,341,542 | 9/1967 | LeSuer et al. | 544/243 |
| 3,977,981 | 8/1976 | Dunlop et al. | 252/8.55 |
| 4,144,181 | 3/1979 | Elliott et al. | 252/33 |

FOREIGN PATENT DOCUMENTS

| | | | |
|---|---|---|---|
| 0193973 | 9/1986 | European Pat. Off. | 544/242 |
| 1253817 | 1/1961 | France . | |
| 740936 | 8/1953 | United Kingdom . | |
| 1010568 | 11/1965 | United Kingdom . | |

*Primary Examiner*—David B. Springer
*Attorney, Agent, or Firm*—V. T. White

[57] ABSTRACT

There are disclosed macrocyclic and polycyclic polyamide lubricating oil additives formed by cyclodehydration of reaction products of hydrocarbon substituted succinic anhydrides or carboxylic acids with poly 3-amino propyl compounds or by acylation of macrocyclic polyamines and polycyclic polyamines with hydrocarbon substituted succinic anhydride or carboxylic acids. These compounds are useful as dispersants and dispersants-V.I. improvers in both gasoline and diesel engine lubricating oil compositions and are also useful fuel additives.

8 Claims, No Drawings

MACROCYCLIC POLYAMINE AND POLYCYCLIC POLYAMINE MULTIFUNCTIONAL LUBRICATING OIL

This is a continuation of Ser. No. 429,177, filed Oct. 30, 1989, now abandoned, which is a divisional of Ser. No. 902,779, filed Sep. 2, 1986, now U.S. Pat. No. 4,880,923, which is a division of Ser. No. 550,977, filed Nov. 16, 1983, now U.S. Pat. No. 4,637,866 which is a continuation-in-part of application Ser. No. 453,143, filed Dec. 27, 1982, now abandoned which in turn is a continuation in pat of application Ser. No. 415,980 filed Sep. 8, 1982, now abandoned which is a division of Ser. No. 243,781 filed Mar. 16, 1981, now abandoned which is a continuation of application Ser. No. 67,546 filed Aug. 17, 1979, now U.S. Pat. No. 4,283,857, which is a continuation-in-part of application Ser. No. 817,217 filed Jul. 20, 1977 now U.S. Pat. No. 4,174,322 and application Ser. No. 806,326 filed Jun. 13, 1977 now U.S. Pat. No. 4,167,514, both of which are divisional applications of Ser. No. 726,206 filed Sep. 24, 1976, now U.S. Pat. No. 4,062,786.

This invention relates to novel lubricating oil additives and lubricating oil compositions containing same which exhibit the desirable properties of being mulifunctional dispersants and viscosity index improvers for both gasoline and diesel engine formulations. More particularly, the invention relates to amine derivatives of oil soluble hydrocarbon substituted succinic anhydrides which are characterized by a macrocyclic or polycyclic polyamine structure resulting from the use of certain 3-aminopropyl compounds in a cyclodehydration reaction or from reaction with certain preformed cyclic amino compounds.

Lubricating oil additives, especially dispersants prepared by the reaction of hydrocarbon substituted succinic acid anhydrides with polyamines, to give linear mono- and bis-imides, are well known in the art and representative disclosures include U.S. Pat. No. 3,172,892 issued Mar. 9, 1965 to LeSuer et al. U.S. Pat. No. 3,272,746, issued Sep. 13, 1966 to LeSuer et al. Patents which disclose a cyclic structure for the dispersant additive include U.S. Pat. No. 4,102,798 issued Jul. 25, 1978 to Ryer et al and U.S. Pat. No. 4,239,636 issued to Brois which discloses a product containing a macrocyclic lactone ester.

Dispersant viscosity index (VI) improvers which result from the grafting of maleic anhydride to an ethylene propylene copolymer with subsequent reaction with polyamines are also known and are disclosed; for example, in U.S. Pat. No. 4,089,794 issued May 16, 1978 to Engel et al and U.S. Pat. No. 4,144,181 issued Mar. 13, 1979 to Elliot et al. The present invention is considered distinguished from the foregoing Engel et al and Elliot et al patents through formation of the characteristic macrocyclic polyamine structure.

U.S. Pat. No. 4,160,739 teaches that the reaction between polyamines and grafter maleic anhydride polymers, only one reactive amine group must be present in the polyamine to eliminate interfering reactions. U.S. Pat. No. 4,137,185 teaches that, in the reaction between the same materials, alkylene polyamines having two primary amine groups produce linear amino-imides which can cause adverse increases in viscosity, and, therefore, acylation of $NH_2$ groups in the amino-imide products with anhydrides is required to prevent chain extension.

One aspect of the present invention is based upon the discovery that certain macrocyclic and polycylic polyamine compounds posses significant properties as multifunctional dispersant-viscosity index improvers, especially the capability to be a highly effective dispersant in both a gasoline engine lubricating oil formulation and corresponding diesel engine lubricating oil formulations and thereby enable lubricating oils containing these novel additives to pass or exceed the highest qualification standards for such oils.

In accordance with one embodiment of this invention there have been discovered as novel compositions of matter oil-soluble, macrocyclic polyamine compounds being the reaction product, in a cyclodehydration reaction, of a hydrocarbon substituted succinic anhydride with a poly 3-amino propyl amine compound, having 2 to 8 nitrogen atoms, the oil soluble macrocyclic polyamine compound being a member of the group of compounds represented by the following formulas, or mixtures of said compounds:

I

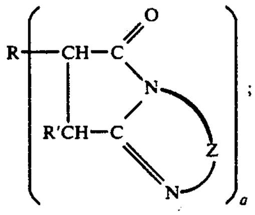

;

II

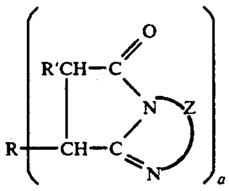

; or

III

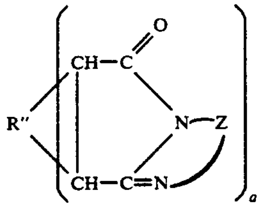

wherein R' is hydrogen or lower $C_1$-$C_{12}$ alkyl, R is a hydrocarbon substituent having 2 to 15,000 carbon atoms, R'' is a hydrocarbon substituent of 4 to 15,000 carbon atoms having two of its carbon atoms bonded to the alpha carbon atoms of the cyclodehydrated succinic anhydride moiety, Z may represent $-CH_2CH_2CH_2-$, $-(CH_2CH_2CH_2NH)_nCH_2CH_2CH_2-$ where n is 1-6 or $-(CH_2CH_2CH_2NH)_mCH_2(CH_2)_p(NH-CH_2CH_2CH_2)_{m'}-$ where m and m' are each at least 1 and m+m' is 2-5, p is 1-4 and a is an integer 1-20.

Formulas I and II above are meant only to represent different isomers which will form as result of formation of the hydrocarbon substituted succinic anhydride. A typical product will be a mixture of isomers such as about 50-90% of the Formula I syn-isomer and the balance the Formula II antiisomer. Formula III would be illustrated by a Diels-Alder type reaction in the preparation of polyisobutenyl succinic anhydride from chlorinated polyisobutylene and maleic anhydride where two reactive sites are provided for bonding the polymer backbone to each of the alpha carbon atoms of the anhydride moiety.

With reference to Formula I above the simplest embodiment would be represented by a formula wherein Z is trimethylene and a is 1:

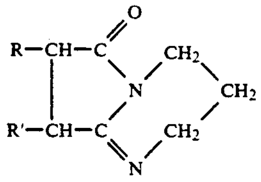

and this compound would therefore be derived from 1,3-propanediamine.

Larger macrocyclic structures can be represented by the structure below wherein Z is $—CH_2CH_2CH_2NHCH_2CH_2CH_2—$ and a is 1:

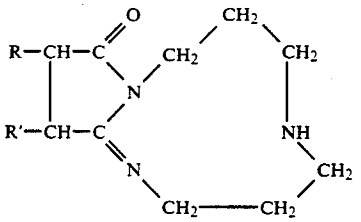

and in the next structure below, a is 1, and Z is a polyimino alkylene unit of the formula $—(CH_2)_3—NH—(CH_2)_3—NH—(CH_2)_3\text{-}NH(CH_2)_3NH—(CH_2)_3—$:

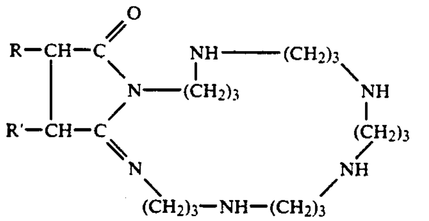

The variation of a between 1 and 20 is intended for numbers greater than 1 to represent multi-site macrocyclic polyamines, that is, those products derived from polyfunctionalized hydrocarbon succinic anhydrides having more than 1 succinic anhydride group per mole of hydrocarbon substituent. Usually, such as for ethylene-propylene copolymer substituted succinic anhydrides, the value of a may vary from about 1 to about 10. The preferred value is about 1 to 8, with multi-site products derived from ethylene propylene copolymers and terpolymers of $M_n$ 10,000 to 200,000 being particularly preferred with a corresponding preferred value for a of from about 2 to 20 since these products have good viscosity modifying or viscosity index improving properties.

In another embodiment of the invention macrocyclic polyamine compounds may also be formed in the same cyclodehydration reaction using the inverse addition process except the intermediate formed is a 1:1 amine carboxylate salt which is subsequently cyclodehydrated utilizing the same category of poly(3-aminopropyl) amine reagents from monocarboxylic acid to give macrocyclic compounds having the general formula:

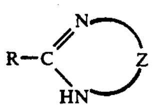

wherein R and Z are as described above. Similarly, useful macrocyclic polyamine compound may be prepared from polycarboxylic acids or polymers such as ethylene-propylene graft copolymer with acrylic acid or alternating copolymers of ethylene-acrylic acid or vinyl ether-acrylic acid in accordance with the cyclodehydration reaction process of the invention to give macrocyclic compounds which may be generalized as

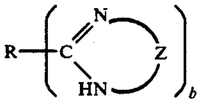

wherein b is an integer of 2 or more representing compounds derived from polycarboxylic acids having 2 or more reactive carboxylic groups. The upper limit of b is a value of about 150. R and Z are as previously defined. These embodiments differ structurally from those macrocyclic polyamines derived from the hydrocarbon succinic anhydrides but the cyclodehydration reaction process and poly(3-aminopropyl) amine reagents useful therein are the same.

These embodiments of the present invention depend upon the use of polyamines having terminal 3-amino propyl groups including both simple diamines such as 1,3-propane diamines, 3,3'-imino-bis-propylamine, N,N-bis-(3-amino propyl)ethylene diamine and higher oligomers such as pentapropylene hexamine. Further embodiments include polyamino propyl amines having C-substituents such as $C_{12}$–$C_{20}$ alkyl, $C_6$–$C_{10}$ aryl, hydroxyl, thiol, cyano, ethoxy, polyoxyethylene and polyoxypropylene having a degree of polymerization of 2–10 and other compatible non-reactive functional groups, but N-substituted polyamines are not suitable reactants in preparing the macrocyclic compounds of this invention in a cyclodehydration reaction. Amines not meeting these requirements, such as ethylene, 1,2-propylene amines will, upon aminolysis, give non-cyclic imide type products not within the scope of this invention as opposed to the macrocyclic structures obtained in accordance with the invention, the cyclic structure being the essential critical aspect of this invention.

Suitable amines for the cyclodehydration reaction may be generalized by the formula $NH_2\text{-}Z\text{-}NH_2$, where Z is as described above. The carbon atoms may contain substituents as noted above but the nitrogen atoms must be either —NH or $—NH_2$. Preferably Z is $—CH_2CH_2CH_2^-$, $—(CH_2CH_2CH_2NH)_nCH_2CH_2CH_2^-$ where n is 1-3 or $—(CH_2CH_2CH_2NH)_m$ $(CH_2CH_2)$ $(NHCH_2CH_2CH_2^-)_{m'}$ where m and m' are as described above.

Formation of the macrocyclic and polycyclic polyamine compounds of the present invention proceeds by aminolysis of the hydrocarbyl substituted succinic anhydride, monocarboxylic acid or polycarboxylic acid using an inverse mode of addition. Such a process will avoid the formation of the prior art non-cyclic, imide products or other products resulting from chain extension. The first step of the synthesis is to slowly add the succinic anhydride or mono- or polycarboxylic acid to the polyamine compound at relatively low temperatures, such as room temperature, that is, about 20° C., up to about 100° C. in an inert hydrocarbon solvent, such as xylene, toluene, dichlorobenzene or a neutral paraffinic mineral oil. This inverse mode of addition is critical to form the 1:1 amic acid or amine carboxylate salt intermediate and inhibit or prevent formation of imide or bis-imide non-cyclic final products. The reaction temperature during this inverse addition of hydrocarbon succinic anhydride or carboxylic acid should be as low as possible, preferably below 100° C., and the optimum temperature will vary somewhat depending on the reactivity and structure of the anhydride compound. The first phase is believed to be the formation of an intermediate and the temperature and rate of addition should be merely sufficient to promote this reaction. Thus at the beginning of the reaction a molar excess of amine relative to moles of succinic anhydride or carboxylic acid groups present is used to minimize any chain extension or bis-imide formation. The formation of an intermediate 1:1 amic acid salt is indicated by the disappearance of carbonyl bands in the infrared spectrum of the anhydride reactant. The formation of the amine carboxylate intermediate is indicated by the appearance of a carbonyl band in the infrared spectrum of the product due to carboxylate formation.

The second step of the process, the cyclodehydration of the amic acid or amine carboxylate intermediate is effected at a temperature consistent with the reactivity of the intermediate salt, with suitable cyclodehydration temperatures ranging from 130° C.-250° C., preferably about 140° C. to 175° C. Formation of the macrocyclic polyamine structure is indicated by cessation of evolution of water and by the maximization of the C=N absorption band at about the 6 micron range in the infrared spectrum of the reaction product.

It is critical to the cyclodehydration process of the present invention that this inverse mode of addition be used to effect the aminolysis of the succinic anhydride or carboxylic acid. Thus the slow addition of hydrocarbon succinic anhydride or carboxylic acid to the well stirred polyamine, preferably in solution, maintained at about 20° to 100° C. maximizes the formation of the 1:1 intermediate salt which upon further heating at 130°-250° C. undergoes cyclodehydration to the desired macrobicyclic polyamine product. In contrast to this, the prior art mode of addition, such as adding the polyamine to the hydrocarbon succinic anhydride, produces linear imide products.

The yield of macrocyclic polyamine lubricating oil additive products formed in accordance with the cyclodehydration process of this invention will vary somewhat from about 50% to 90% depending on various parameters including reactants used, temperatures, rate of addition and whether laboratory, pilot or commercial process procedures are being conducted. The balance of the products produced will generally be the bis-imide reaction products which in most cases can be tolerated in the final product since they are known lubricating oil additives, but it is preferred that such by-products not exceed about 30% yield and that the yield of desired macrocyclic polyamine additive be on the order of about 70% or more.

A preferred technique for preparing the macrocyclic and polycyclic polyamine compounds in accordance with this invention and improving the yield thereof comprises the additional step of heat soaking the reaction mixture subsequent to the addition of the hydrocarbyl substituted succinic anhydride, mono- or polycarboxylic acid by maintaining the reaction mixture at a temperature of 80° to 130° C. for 1 to 3 hours and prior to increasing the temperature to effect the cyclodehydration reaction. After the conclusion of the heat soak period, the temperature of the reaction mixture is increased to the cyclodehydration range of 130° to 250° C. but at least 20° C. higher than the temperature employed during the heat soaking step.

For preparation of preferred embodiments of this invention using polyisobutenyl succinic anhydride of Mn about 900 to 2,000, it is preferred to conduct the inverse addition step at a temperature of about 75° to 85° C., such as 80° C., then heat soak the reaction mixture at about 80° C. to 110° C. for 3 hours and thereafter effect the cyclodehydration by increasing the reaction mixture to 175° to 180° C. and maintaining this temperature for about 10 hours.

The use of acid catalysis has also been found to be a preferred process technique for improving the yield of the products of this invention. Preferred are oil soluble strong acids such as alkyl aryl sulfonic acids such as alkyl benzene sulfonic acid of about Mn 300 to 800, a $C_{24}$ alkyl benzene sulfonic acid being especially preferred. Also suitable are alkyl sulfonic acids, organic phosphoric acids, resin acids as well as the mineral acids such as HCl and $H_2SO_4$. In general the acid should have a pKa of about $-100$ to $+5$. The acid will be employed by adding it to the polyamine prior to inverse addition in mole ratios of 1:1 to 1,000:1 moles of amine per mole of acid.

The hydrocarbon substituted succinic anhydrides which are suitable for reaction with the poly 3-amino propyl reagents or pre-formed cyclic amines in accordance with this invention are derived generally from oil soluble hydrocarbons comprising unbranched saturated or unsaturated hydrocarbon chains of at least 8, preferably at least 50 carbon atoms including both polymeric, oligomeric and nonpolymeric aliphatic chains, particularly polymers of $C_2$—$C_5$ olefins. Particularly preferably for use in this invention is thermal polyisobutenyl succinic anhydride of Mn about 900 to 2,000 butylene and maleic anhydride at about 200° C. Hydrocarbon substituents having from about 8 to 50 carbon atoms, while forming useful oil-soluble products, are less preferable as dispersant viscosity index improvers. They have been found, however, to exhibit desirable properties as antioxidants in oleaginous compositions, such as products of the present invention derived from octadecenyl succinic anhydride.

Suitable olefin polymers include polymers comprising a major molar amount of $C_2$ to $c_5$ mono olefins, e.g., ethylene, propylene, butylene, isobutylene and pentene. The polymers may be homopolymers such as polyisobutylene, as well as copolymers of two or more such olefins such as copolymers of ethylene and propylene, butylene and isobutylene, propylene and isobutylene and the like. Other copolymers include those in which a minor molar amount of the copolymer monomers, e.g., 1-20 mole %, is a $C_4$ to $C_{18}$ non-conjugated diolefin, e.g., a copolymer of ethylene, propylene and 1,4-hexadiene, i.e. the EPDM polymers.

The olefin polymers will usually have number average molecular weight within the range of about 500 to about 200,000, more usually to about 60,000. Particularly useful olefin polymers for dispersant additives have number average molecular weights (Mn) within the range of about 900 to about 2,000 with approximately one terminal bond per polymer chain. Especially useful material in the present invention is polyisobutylene. Polybutene-1 and polypropylene are also preferred hydrocarbon substituents for preparing dispersants.

Particularly useful materials, when dispersant-viscosity index improving additives are desired, are derived from ethylene, propylene copolymers, terpolymers and tetrapolymers having a $M_n$ of about 10.,000 to 200,000, especially 25,000 to 100,000. An example is a copolymer of about 30 to 85 mole % ethylene, 15 to 70 mole % $C_3$ to $C_5$ mono-alphaolefin, preferably propylene, and 0 to 20 mole % of a $C_4$ to $C_{14}$ non-conjugated diene. Preferred examples of such dienes include those of U.S. Pat. Nos. 3,790,480; 4,089,794 and 4,137,185. Particularly useful dienes are 5-ethylidene norbornene; 1,4-hexadiene; 2,5-norbornadiene and ethyl norbornadiene. The latter terpolymers are commercially available under the trademarks VISTALON® an elastomeric terpolymer of ethylene, propylene and 5-ethylidene norbornene, marketed by Exxon Chemical Company and NORDEL® a terpolymer of ethylene, propylene and 1,4-hexadiene, marketed by E. I. DuPont de Nemours and Company the term copolymer is used herein is meant to include terpolymers and tetrapolymers.

Other useful hydrocarbon substituents include styrene-isoprene copolymers, styrene-isobutene copolymers, isobutene-butadiene-1,3 copolymers, propene-isoprene copolymers, isobutene-chloroprene copolymers, isobutene(para-methyl)styrene copolymers, copolymers of hexene-1 with hexadiene-1,3, copolymers of octene-1 with hexene-1, copolymers of heptene-1 with pentene-1, copolymers of 3-methyl-butene-1 with octene-1, copolymers of 3,3-dimethylpentene-1 with hexene-1, and terpolymers of isobutene, styrene and piperylene. More specific examples of such interpolymers include copolymer of 95% (by weight) of isobutene with 5% (by weight) of styrene; terpolymer of 98% of isobutene with 1% of piperylene and 1% of chloroprene; terpolymer of 95% of isobutene with 2% of butene-1 and 3% of hexene-1; terpolymer of 60% of isobutene with 20% of pentene-1 and 20% of octene-1; copolymer of 80% of hexene-1 and 20% of heptene-1; terpolymer of 90% of isobutene with 2% of cyclohexene and 8% of propylene.

Techniques for attaching succinic anhydride groups to the above-described hydrocarbons and polymers are well known in the art and these include, for example, reacting maleic anhydride directly with the polyolefin which may have first been halogenated in the range of about 2 to 5 wt. % prior to the reaction of maleic anhydride. Grafting of maleic anhydride with ethylene propylene copolymers and terpolymers is described in U.S. Pat. Nos. 4,089,794 and 4,137,185 and represents a particularly preferred embodiment since it provides a multi-site reactant which, upon aminolysis and cyclodehydration in accordance wit the invention, results in a lubricating oil additive having especially valuable multi-functional dispersant-viscosity index improving properties and such products are especially useful in improving the dispersancy of diesel engine oil formulations.

In another embodiment of the present invention macrocyclic and polycyclic polyamine additives can be prepared by condensing the hydrocarbon succinic anhydrides with macrocyclic polyamines (aza crown compound) and polycyclic polyamines (aza polycycles) in an acylation reaction. Aza crown compounds useful herein are those having at least 2NH groups and may be represented by the formula:

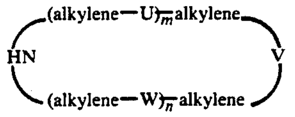

wherein U,V and W can be NH, S and/or O, n or m is an integer of 1 to about 4, alkylene is $C_2$-$C_4$, usually an ethylene or trimethylene group, and these aza crown compounds include macrocyclic polyamines (U=V=W=NH), polyether amines; U=W=O, V=NH, etc.) and polythioether amines; U=W=S; V=NH).

Examples within the scope of the foregoing formula are macrocyclic polyamines and their complexes having three to about eight nitrogen atoms, at least one, which is an NH group, Preferred are those having four nitrogen donors in cycles containing about 12 to 16 atoms. Examples of useful macrocyclic polyamines include 1,4,8,11-tetraazacyclo-tetradecane (cyclam), 1,4,7,10-tetrazacyclododecane, 1,4,7, 10-tetraazacyclotridecane, 1,4,8,12-tetraazacyclopentadecane, 1,5,9,13-tetraazacyclohexadecane, and 1,4,7,10,13, 16-hexaazacyclooctadecane (hexacyclen).

Also suitable are mixed donor macrocyclic amines containing nitrogen-oxygen, nitrogen-sulfur, and nitrogenoxygen-sulfur donor groups as depicted below which can be acylated to give useful lubricant additives.

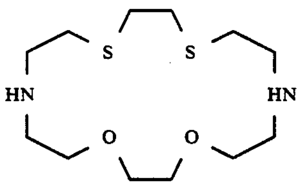

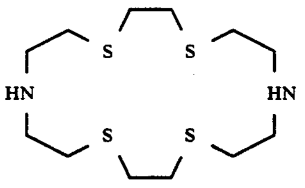

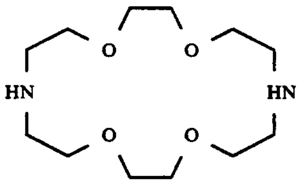

Also useful are aza polycyclic ring assemblies aza polycycles) containing 2 to 3 rings having 5 to 6 atoms in the ring, including 3 or 4 nitrogen atoms at lease one being an NH group, but preferably 2-3 NH groups per molecule are present, which compounds can be represented by the formulas:

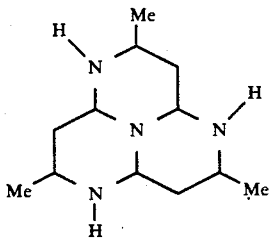

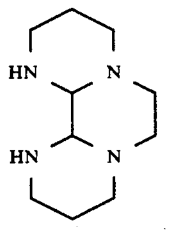

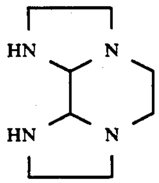

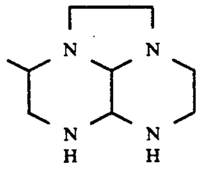

These amino compounds may be acylated by reacting at least a half-mole equivalent up to a 2 mole equivalent of the aforementioned hydrocarbon substituted succinic anhydrides to yield useful lubricant additives.

Further embodiments of the present invention reside in the formation of metal complexes and other post-treatment derivatives, e.g. borated derivatives, of the novel macrocyclic additives prepared in accordance with this invention. Suitable metal complexes may be formed in accordance with known techniques of employing a reactive metal ion species during or after the reaction of the polyamine and the hydrocarbyl anhydride compound. Complex-forming metal reactants include the nitrates, thiocyanates, halides, carboxylates, phosphates, thio-phosphates, sulfates, and borates of transition metals such as iron, cobalt, nickel, copper, chromium, manganese, molybdenum, tungsten, ruthenium, palladium, platinum, cadmium, lead, silver, mercury, antimony and the like. Prior art disclosures of these complexing reactions may be found in U.S. Pat. Nos. 3,306,908 and Re. 26,433.

Post-treatment compositions include reacting the novel macrocyclic additives of the present invention with one or more post-reacting reagents, usually selected from the group consisting of boron oxide, boron oxide hydrate, boron halides, boron acids, sulfur, sulfur chlorides, phosphorous sulfides and oxides, carboxylic acid or anhydride acylating agents, epoxides and episulfides and acrylonitriles. The reaction of such post-treating agents with the novel macrocyclic polyamine compounds of this invention is carried out using procedures known in the art. For example, boration is accomplished in accordance with the teachings of U.S. Pat. Nos. 3,254,025 by treating the macrocyclic polyamine compound with a boron oxide, halide, ester or acid to provide about 0.1 to 1 atomic proportions of born for each atomic proportion of nitrogen in the composition. Treatment is carried out by adding about 1-3 wt % of boron compound, preferably boric acid, and heating and stirring the reaction mixture at about 135° C. to 165° C. for 1 to 5 hours followed by nitrogen stripping and filtration, if desired. Mineral oil or inert organic solvents facilitate the process.

A particularly preferred post-treatment technique especially useful for preparation of lubricating oil dispersants is post-treatment with a polyisobutenyl succinic anhydride. In this embodiment a polyisobutenyl succinic anhydride-poly 3-aminopropylamine macrobicyclic reaction product is first prepared in accordance with the invention, and subsequently treated with about 10–50 mole % of additional polyisobutenyl (Mn of about 900–2000) succinic anhydride at elevated temperatures of about 120° C. for about one hour or until the reaction mixture shows complete reaction of the free anhydride. Such products are especially useful as dispersants for diesel engine lubricating oil compositions.

The products of this invention can be incorporated in lubricating oil compositions, e.g., gasoline or diesel crankcase lubricating oil in active ingredient concentrations within the range of about 0.01 to 20 wt % based on the total weight of the lubricating oil composition. Such additives are usually dispensed in the form of concentrates as discussed below.

The products prepared according to this invention can be incorporated in a wide variety of lubricants. They can be used in lubricating oil compositions, such as automotive crankcase lubricating oils, automatic transmission fluid, etc., in active ingredient concentrations generally within the range of about 0.5 to 10 wt %, for example, 1 to 5 wt. %, preferably 1.5 to 3 wt. % of the total composition when used only as a dispersant. Conventionally, the dispersants are admixed with the lubricating oils as concentrates which usually contain up to about 50% weight of the additive compound dissolved in mineral oil, preferably a mineral oil having an ASTM D-445 viscosity of about 2 to 40, preferably 5 to 20 centistokes at 99° C. The lubricating oil includes not only hydrocarbon oils derived from petroleum but also includes synthetic lubricating oils such as polyethylene oils; alkyl esters of dicarboxylic acids, complex esters of dicarboxylic acid, polyglycol and alcohol; alkyl esters of carbonic or phosphoric acids; polysilicones; fluorohydrocarbon oils; and, mixtures of lubricating oils and synthetic oils in any proportion, et. The term, "lubricating oil" for this disclosure includes all the foregoing. The useful additive of this invention may be conveniently dispensed as a concentrate of 10 to 80 wt. % such as about 49 wt. % of said dispersant in 20 to 90 wt. % of mineral oil, e.g., Solvent 150 Neutral oil with or without other additives being present.

As noted above, such composition or concentrates containing the dispersants of the present invention will also contain other well-known additives such as the zinc dialkyl ($C_3$–$C_8$) dithiophosphate anti-wear inhibitors usually present in amounts of from 1 to 5 wt. %.

Useful detergents include the normal basic or overbased metal, e.g., calcium magnesium, barium, etc., salts of petroleum naphthene acids, petroleum sulfonic acids, alkyl benzene sulfonic acids, oil-soluble fatty acids, alkyl salicyclic acids, alkylene bisphenols and hydrolyzed phosphosulfurized polyolefins. Typical amounts are from 1–7 wt. % with preferred materials being normal and basic calcium and magnesium sulfonates, phenates and sulfurized phenates.

Oxidation inhibitors include hindered phenols, e.g., 2,6-ditert-butyl para-cresol, amines, sulfurized phenols and alkyl phenothiazines, usually present in amounts of from 0.001 to 1 wt. %.

Pour point depressants usually present in amounts of 0.01 to 1 wt. % include wax alkylated aromatic hydrocarbons, olefin polymers and copolymers, acrylate and methacrylate polymers and copolymers.

Viscosity index improvers including olefin polymers and copolymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl pyrrolidone or dimethylaminoalkyl methacrylate, post-grafted polymers of ethylenepropylene with an active monomer such as maleic anhydride which may be further reacted with an alcohol or an alkylene polyamine, styrene/maleic anhydride polymers post-treated with alcohols and amines, etc. Such products are used in amounts as required to meet the viscosity grade desired, generally 1-15 wt. % being used.

Rust inhibition activity can be provided by the aforementioned metal dihydrocarbyl dithiophosphates and the corresponding precursor esters, phosphosulfurized pinenes, sulfurized olefins and hydrocarbons, sulfurized fatty esters and sulfurized alkyl phenols. Preferred are the zinc dihydrocarbyl dithiophosphates with are salts of dihydrocarbyl ($C_3$-$C_8$) esters of dithiophosphoric acids. Rust inhibitors are usually used in the range of 0.01 to 1 wt. %.

Fuel economy or friction reducing additives may also be present such as dimer acid esters with glycols as disclosed in U.S. Pat. No. 4,105,571 issued to Shaub with the esters of dimerized linoleic acid and diethylene glycol being a preferred material or other effective fuel economy additives such as glycerol esters of $C_{16}$-$C_{18}$ fatty acids with glycenol oleate being especially suitable. These additives are present in amounts which vary greatly according to their effectiveness but generally are used in very small proportions.

Thus, the term lubricating oil composition as used herein is meant to include an oil of lubricating viscosity containing in addition to the products of this inventions conventional additives in customary amounts as required to provide their normal attendant functions.

The macrocyclic polyamine and polycyclic polyamine compounds of this invention may also be used in fuels in amounts sufficient to provide dispersant and detergent properties to the fuel, particularly in preventing and removing deposits from the carburator and fuel lines when used preferably in gasoline fuel composition. The compounds of the invention may be used in fuels in amounts ranging from about 0.001 to about 1 wt. %, preferably about 0.0004 to about 0.1 wt. % based on the weight of the fuel composition. Suitable fuel compositions include normally liquid hydrocarbon fuels such as motor gasoline (ASTM D439-73) diesel fuel or fuel oil (ASTM D-391) and mixtures of such hydrocarbon fuels with non-hydrocarbon materials such as alcohols, ethers, nitro compounds and the like.

The invention is further illustrated by the following examples which are not to be considered as limitative of its scope.

One aspect of the present invention teaches the aminolysis of succinic anhydride functionality attached to a hydrocarbon or substituted hydrocarbon chain of any length by purposely adding the hydrocarbon succinic anhydride to a 3-aminoalkyl substituted amine such as 3-amino-propylamine, 3-amino-2-hydroxy-propylamine, N,N'-bis(3-aminopropyl) ethylene-1,2-diamine, or an oligomeric poly-1,3-propylene polyamine. This inverse mode of addition at 0°-140° C. converts the anhydride group into a 1:1 molar succinamic acid amine salt adduct which upon heating neat or in a suitable azeotroping solvent, e.g. xylene, undergoes cyclodehydration to give a hydrocarbon chain bearing bicyclic and/or macrobicyclic polyamine functionality.

The following examples in groups (A), (B) and (C) teach the inverse addition route to bicyclic and macrobicyclic polyamines from (A) low molecular weight hydrocarbon succinic anhydrides (HSA) ranging from nadic anhydride to n-octadecenyl anhydride (B) intermediate molecular weight HSA (Mn 500-10,000) such as polyisobutenyl succinic anhydrides useful for dispersant synthesis, and (C) polymers (Mn 10,000 and higher) bearing more than one succinic anhydride per chain useful for designing dispersant VI improvers.

To emphasize the remarkable sensitivity of product composition to mode of addition, the prior art method, i.e. the addition of polyamine to hydrocarbon succinic anhydride (direct addition) is also described to illustrate the formation of linear imide product as taught in the prior art.

A. SYNTHESIS OF LOW MOLECULAR WEIGHT MACROBICYCLIC POLYAMINES

EXAMPLES

EXAMPLE A1

8-Octadec-2-Enyl-2,6-Diaza-Bicyclo[4.3.0]Non-1-En-7-One Via Aminolysis of Octadecenyl-Succinic Anhydride (OSA) With 1,3-Propanediamine (PDA)

Approximately 1.5 moles (112 g) of PDA was dissolved in a half liter of isopropanol contained in a reactor fitted with a Dean-Start trap. To the stirred solution at about 25° C. was added dropwise 1.02 mole (357 g) of OSA dissolved in a liter of tetrahydrofuran. Following addition, the solvents were distilled off and gradually replaced by xylene. The reaction mixture was refluxed until no more water collected in the Dean-Stark trap (about 8 hours). upon cooling overnight, solid separated from the xylene solution. Filtration gave a high yield of product which featured an IR spectrum displaying a prominent C═N absorption band at 6 microns, and analyzed for 77.15% C, 11.53% H, and 7.06% N. Theory for the title compound ($C_{25}H_{45}N_2O$) requires 77.26% C, 11.41% H and 7.21% N. Attempts to aminate OSA with ethylene diamine in the manner described above gave aminoimide product exclusively.

EXAMPLE A2

Preparation of 12-$_n$-Octyl-2,6,10-Triaza-Bicyclo[8.3.0]-Tridec-2-En-11-One Via Aminolysis of n-Octylsuccinic Anhydride With 3,3-Imino-Bis-Propylamine (IBPA)

To a mixture of 14.7 g (0.11 mole) of 3,3'-iminobispropylamine in 350 ml of refluxing xylene contained in a reactor equipped with a moisture trap was added 21.2 g (0.10 mole) of n-octyl succinic anhydride in 150 ml of xylene dropwise over a period of six hours. During this period, approximately 2 ml of water were collected in the moisture trap.

After refluxing the reaction mixture for about 8 hours, an additional 2 ml of water were collected. Removal of the xylene solvent by distillation afforded the title macrobicyclic polyamine product and/or its positional isomer isolated in over 80% yield. The liquid product featured an infrared spectrum with a strong absorption band at about 6 microns (characteristic C═N stretching frequency) and analyzed for 13.28% N. Theory for the title compound ($C_{18}H_{33}N_3O$) requires 13.67% N. Attempts to aminate $_n$-octyl succinic anhydride with diethylene triamine in the manner described above afforded linear amino-imide product exclusively.

EXAMPLE A3

15-Octadec-2-Enyl-2,6,9-13-Tetraazabicyclo[11.3.0-]Hexadec-1-En-14-One

To a mixture of 17.6 g (0.101 mole) of 4,7-diazadecane-1,10-diamine in 200 ml of refluxing xylene was added 35.5 g (0.101 mole) of n-octadecenyl-succinic anhydride (OSA) in 175 ml of xylene dropwise over a period of about four hours. After addition of the OSA reactant, the mixture was refluxed for about two hours. Infrared analysis of the reaction mixture revealed macrobicylic polyamine formation was progressing as evidenced by an absorption band appearing at 6.0 microns (C=N stretching frequency). After 10 hours of refluxing, 270 ml of xylene were removed. The mixture was again refluxed for four hours at about 150° C. The IR spectrum of the mixture revealed a very strong absorption band at 6.0 microns, indicating that macrocycle formation was maximized. The solvent was removed under vacuum, and the residue was sparged with nitrogen at 150° C. for about two hours. The title compound and/or its positional isomer (with the n-octadecenyl group at position 16) was isolated in 88% yield (44.7 g). The product analyzed for 73.19% C, 11.31% H, and 11.38% N. Analysis calculated for $C_{30}H_{57}N_4O$ requires 73.62% C, 11.65% H and 11.45% N.

EXAMPLE A4

16-Octadec-2-Enyl-2,6,10,14-Tetraazabicyclo[12.3.0-]Hepta-Dec-1-En-15-One Via Aminolysis of $_n$-Octadecenyl-Succinic Anhydride (OSA) With 4,8-Diazaundecane-1,11-Diamine (DUDD)

A sample of DUDD weighing 38.25 g (0.203 mole) was dissolved in 350 ml of xylene and brought to reflux in a reactor fitted with a Dean-Stark moisture trap. To the stirred refluxing solution was added dropwise over six hours 71.2 g (0.203 mole) of OSA dissolved in 250 ml xylene. After about 8 hours refluxing, a total of 6.6 ml of water was collected. The reaction temperature was increased to 160° C. and the remaining solvent was removed by nitrogen sparging for several hours. The macrobicyclic product (96 g isolated) showed an IR spectrum with a prominent absorption band at 6 microns, and analyzed for 73.65% C, 11.58% H, and 10.63% N. Theory for the title compound ($C_{31}H_{59}N_4O$) requires 74.0% C, 11.73% H, and 11.13% N.

EXAMPLE A5

23-Octadec-2-Enyl-2,6,10,13,17,21-Hexaza-Bicyclo[19.3.0]Tetracos-1-En-22-One Via Aminolysis of $_n$-Octadec-2-Enyl Succinic Anhydride (OSA) with 4,8,11,15-TetraAzaoctaDecane-1,18-Diamine(TADD)

Crude TADD was distilled through a 30 cm column (1 inch O.D.) of glass beads under vacuum. A constant boiling fraction, b.p. 207° C. (1 mm) was collected. Analysis by mass spectrometry showed the fraction to be 85% TADD, 10% 4,8,11-triazatetradecane-1,14-diamine and 5% 4,8,11,15,19-pentazadocosane-1,22-diamine. A 30.2 g (0.105 mole) sample of this fraction was dissolved in 250 ml of boiling xylene. To the refluxing xylene solution of TADD was added 35 g (0.10 mole) of OSA dissolved in 250 ml xylene over a period of 9 hours. The water of reaction was collected in a moisture trap fitted on the reactor. The mixture was refluxed for about 14 hours, and then concentrated under reduced pressure. Sparging the concentrate with nitrogen at 100° C. for 2 hours gave 59.2 g of product (90% yield of macrobicyclic polyamine) which featured an IR spectrum having a prominent absorption band at 6 microns, and analyzing for 72.73% C, 11.69% H, and 14.87% N. Theory for $C_{36}H_{71}N_6O$ requires 71.64% C, 11.77% H and 13.93% N.

Treatment of 7.12 g (ca. 11.8 millimole) of the title macrobicyclic product dissolved in 50 ml of chloroform with 1.61 g (11.8 millimole) of zinc chloride gave, after 18 hours stirring at room temperature and solvent removal, a brown crystalline solid. The dried product featured a 6.0 micron absorption band in the IR, and analyzed for 57.93% C, 9.20% H, and 9.73% N. Analysis calculated for $C_{36}H_{71}N_6OZnCl_2$ complex requires 58.43% C, 9.60% H and 11.36% N. The Zn complex was soluble in chloroform, methanol and xylene, and insoluble in pentane.

EXAMPLE A6

Synthesis of 3,7-Diaza-Tetracyclo[9.2.1.0$^{1,9}$.0$^{2,7}$]-Tetradeca-1,11-Dien-8-One Via Aminolysis of Nadic Anhydride With 1,3-Propane Diamine Eight moles (592 g) of 1,3-diamine propane dissolved in liter of xylene were charged into a 5 liter 4-necked reactor equipped with a moisture trap, and heated to 115° C. Then, 4 moles (656 g) of nadic anhydride (5-norbornene-2,3-dicarboxylic anhydride) dissolved in 2 xylene were gradually added to maintain steady refluxing. The mixture was held at reflux until water ceased to collect in the moisture trap. Upon cooling overnight, solid separated from xylene solution. Filtration gave some material characterized as imide product. The supernatant was evaporated to a concentrate and then mixed with a liter of hexane. The mixture was heated to give a clear solution, which upon standing gave crystals. Filtration gave a substantial yield of crystalline product which analyzed for 70.18% C, 6.96% H, and 13.81% N. IR and $^{13}C$ NMR spectral data and elemental analysis for the crystalline product are consistent with the title compound.

EXAMPLE A7

Aminolysis of Nadic Anhydride With 1,3-Propane Diamine (PDA) Mono-Para-Toluene-Sulfonic Acid Salt.

A half mole (37 g) of 1,3-propane diamine was acidified with a half mole (95 g) of p-toluene sulfonic acid hydrate in 250 ml of ethyolene glycol and heated to about 160° C. To the stirred solution was added dropwise over a 2 hour period, a half mole (82 g) of 5-norbornene-2,3-dicarboxylic acid anhydride dissolved in 400 ml tetrahydrofuran (THF). At this temperature (160° C.), THF and water of reaction distilled off. After water evolution ceased (ca. 2 hours), the ethylene glycol was removed under vacuum. Addition of 500 ml of acetone to the cooled residue caused the product to precipitate as a white solid. Filtration gave 170 g of product which was recrystallized from methylene chloride-ether solution. The crystalline product had an IR and carbon NMR spectra identical with the p-toluene sulfonate salt made from the title product described in Example A6.

B. SYNTHESIS OF MACROBICYCLIC POLYAMINE DISPERSANTS

Novel macrobicyclic polyamine dispersants with outstanding sludge and varnish control properties can be designed from a diversity of polyalkenyl succinic anhydrides including the preferred polyisobutenyl succinic anhydrides (PIBSA) and heterosubstituted PIBSA reactants. The latter class of acylating agents are obtained by peroxidizing or sulfenylating the carbon-carbon double bond in PIBSA as taught in U.S. Pat. Nos. 4,167,514 and 4,302,395 and subsequently aminating the heterosubstituted PIBSA reagents according to the process of the present invention.

A variety of PIBSA reactants generated by the Ene, Diels-Alder, or free-radical grafting reactions of maleic anhydride with polyisobutene (PIB) and/or chlorinated (PIB) are readily accessible. The aminolysis of several PIBSA reagents effected by the prior art method and the present invention is elaborated in the example below to show that the mode of addition, i.e. PIBSA to polyamine (present invention) or polyamine to PIBSA will very selectively engender macrobicyclic polyamine or linear imide dispersant product, respectively. Moreover, the macrobicyclic polyamine dispersants, when compared with the linear imide products feature superior performance in tests designed to measure sludge and varnish control.

Example B1

Macrobicyclic Polyamine Formation Via Addition of PolyIsobutenylsuccinic Anhydride to 4,7-Diazadecane-1,10-Diamine About 200 g (ca. 0.087 mole) of polyisobutenylsuccinic anhydride (PIBSA) prepared via Ene reaction of polyisobutylene (Mn 1300 by vapor phase osmometry) and maleic anhydride as described by Brois and Gutierrez in U.S. Pat. No. 4,239,636, and having a saponification number of 48.5 were dissolved in 200 ml of toluene. The resulting toluene solution was added dropwise to a stirred solution of 15.1 g of 4,7-diazadecane-1,10-diamine in 100 ml of toluene at room temperature. This specific mode of addition of anhydride to polyamine selectively affords substantial amount of amic acid salts as equimolar adducts of anhydride and polyamine. Once polyamine addition was complete, the reaction mixture was heated to refluxing temperature to achieve the cyclodehydration of the amic acid salt intermediates. The water of reaction was removed by azeotropic distillation into a moisture trap mounted on the reactor. When water evolution ceased, the toluene was distilled off, and the reaction mixture was then heated to about 175° C. and maintained at said temperature for about 9 hours. The reaction mixture was then stripped of residual light ends with a mold stream at nitrogen gas at 175° C. for about a half hour, and subsequently filtered. The infrared spectrum of the filtered product showed a strong absorption band at about 6 microns, which is diagnostic of C=N functionality ascribable to the macrobicyclic polyamine product described in part, as 15-polyisobutenyl-2,6,9,13-tetraaza-bicyclo [11.3.0] hexadec-1-ene-14-one. Said product analyzed for 1.81% N, and 0.09 milliequivalent of primary amine per gram of product.

Example B2

Macrobicyclic Polyamine Formation Via Addition of PIBSA to 4,8-Diazaundecane-1,11-Diamine About 230 g (ca. 0.1 mole) of the PIBSA described in Example B1 were dissolved in 200 ml of toluene, and transferred to a dropping funnel. The toluene solution of the polyamine was added dropwise to a solution of 18.8 g (0.1 mole) of 4,8-diaza-undecane-1,11-diamine in 100 ml of toluene at room temperature. After anhydride addition was complete, the reaction mixture was heated to refluxing temperature. The water of reaction was collected in a moisture trap mounted on the reactor. When water evolution stopped, the toluene was distilled off, and the reaction temperature reached 175° C.

The mixture was stirred at 175° C. for about four hours, sparged with gaseous nitrogen for a half hour to remove any remaining volatile components, and finally filtered. The filtrate analyzed for 1.97% N, and featured an IR spectrum with a strong absorption band at 6.0 microns which is characteristic of the C=N functionality present in the macrobicyclic polyamine product described in part, as 16-polyisobutenyl-2,6,10,14-tetraazabicyclo [12.3.0] heptadec-1-en-15-one.

LINEAR DISPERSANT SYNTHESIS VIA DIRECT ADDITION ROUTE—COMPARATIVE EXAMPLES B3 AND B4

EXAMPLE B3

Linear Polyamine Succinimide Formation Via Addition of 4,7-Diaza-Decane-1,10-Diamine to Polyisobutenyl-succinic Anhydride (1:1 Molar Ratio)

About 200 g (ca. 0.087) mole of the PIBSA described in Example B1 were charged into a reaction flask and heated to 150° C. and stirred under a nitrogen atmosphere. About an equimolar quantity (15.1 g) of 4,7-diaza-decane-1,10-diamine were added dropwise to the neat PIBSA reactant at 150° C. over a 15 minute period. After polyamine treatment, the reaction mixture was sparged with nitrogen gas at 150° C. for about two hours, and subsequently filtered. The filtrate featured an infrared spectrum with a strong imide carbonyl absorption band at about 5.9 microns ascribable to linear polyamine imides of PIBSA. The analyses indicate that the product is a mixture of 1(2-polyisobutenylsuccinimido)-4,7-diazadecane-10-diazadecane. The filtered residue analyzed for 1.93% N, and 0.24 milliequivalent of primary amine per gram of product.

EXAMPLE B4

Linear Polyamine Bis-Imide Via Addition of 4,7-Diaza-Decane-1,10-Diamine to Polyisobutenylsuccinic Anhydride (1:2 Molar Ratio)

About 200 g (ca. 0.087 mole) of the PIBSA described in Example B1 were charged into a reaction flask and heated to about 150° C. and stirred under a nitrogen atmosphere. Thereafter, 7.6 g (ca. 0.043 mole) of 4,7-diaza-decane-1,10-diamine were added dropwise over a 15 minute period while the reaction temperature was maintained at about 150° C. Once the polyamine addition was complete, the reaction mixture was sparged with gaseous nitrogen for about two hours at 150° C. and subsequently filtered. The filtered product featured an infrared spectrum with a dominant imide carbonyl absorption band at about 5.9 microns, analyzed for 1.17% N, and 00.00 meq of primary amine per gram of product. The analytical data are consistent with bisimide product which can be described mainly as 1,10-bis-(2-polyisobutenylsuccinimido)-4,7-diazadecane.

A series of macrobicyclic polyamines designed from a representative spectrum of polyisobutenyl succinic anhydrides using the inverse addition mode of the present invention are described in Table 1. These are Examples B5 through B14 in Table 1 below and were prepared following the procedure of Examples B1 and B2. It is noteworthy that the post-treatment of selected macrobicyclic polyamines with metal salts, boric acid, alkylene oxide and additional polyisobutenyl succinic anhydride (PIBSA) also affords additives having additional multifunctional properties.

Examples B5 and B6—Use of Heat Soak Process in Preparation of Macrocyclic Polyamines

Example B5

About 228 g (~1 mole) of a polyisobutenyl succinic anhydride (PIBSA) of Sap #65 and Mn=1300 obtained via the ene reaction was diluted with solvent 150 neutral mineral oil to a Sap of 49 were added to 18.8 g (~0.1 mole) of 4,8-diazaundecane-1,11-diamine at 80° C. for a period of 15 minutes. The reaction mixture was soaked at 100°-110° C. for 3 hours while stirring under nitrogen blanket. At the end of the third hour the reaction temperature was raised to 175° C. and maintained at this temperature for 10 hours. Thereafter, the product was nitrogen stripped at 150° C. for one half hour and collected. The final product showed an excellent yield of macrocycle as indicated by the strong absorption at 6.0-6.1 micron of the infrared spectrum and analyzed for 1.96% nitrogen.

Example B6

About 262 g of PIBSA of Mn=1300 and Sap No. 103 were added to 31 g of 4,8-diazaundecane-1,11-diamine containing 3 g of 50% a.i. SA 119 (Trademark for alkylaryl sulfonic acid of molecular weight 500) for a period of one half hour at 80° C. When the addition was completed, the reaction mixture was soaked at 80°-100° C. for 3 hours while stirring under a nitrogen blanket. Thereafter, the temperature was raised to 175°-180° C. and kept for 10 hours. At the end of the 10th hour, the reaction temperature was lowered to 150° C. and the reaction mixture was nitrogen stripped for one half hour. The product showed an intense absorption and had characteristics of macrocyclic materials. It analyzed for 2.58% N.

TABLE 1

MACROBICYCLIC POLYAMINE DISPERSANTS (MPD)

| Example | Polyisobutenylsuccinic anhydride (PIBSA) Type[1] | MW[2] | SAP[3] | Polyamine | MPD % N |
|---|---|---|---|---|---|
| B5 | Thermal | 1300 | 65 | 4-azaheptane-1,7-diamine (AHD) | 1.46 |
| B6 | Chloro | 1300 | 103 | AHD | |
| B7 | Thermal | 1300 | 65 | 4,7-diazadecane 1,10-diamine (DADD) | 1.98 |
| B8 | Thermal | 1300 | 65 | DADD | 1.57 |
| B9 | Thermal | 1300 | 65 | DADD | 1.83 |
| B10 | Grafted | 1300 | 65 | DADD | 2.31 |
| B11 | Chloro | 2300 | 67 | DADD | — |
| B12 | Thermal | 1300 | 65 | 4,8,11,15-te-tetraazaoctadecane-1,18-diamine (TAOD mixture)[4] | 2.54 |

TABLE 1-continued

MACROBICYCLIC POLYAMINE DISPERSANTS (MPD)

| Example | Polyisobutenylsuccinic anhydride (PIBSA) Type[1] | MW[2] | SAP[3] | Polyamine | MPD % N |
|---|---|---|---|---|---|
| B13 | Grafted | 1300 | 65 | TAOD mixture | — |

[1]The preparation of the requisite PIBSA reactants is described in U.S. Pat. Nos. 3,306,908; 4,239,636 and U.K. Patent 1,398,000. Grafted PIBSA can be obtained by reacting a polyisobutene (PIB) and maleic anhydride in the presence of an organic peroxide at an elevated temperature according to Example 1 of U.K. Patent 1,398,000. Chloro PIBSA is prepared by heating chlorinated PIB and maleic anhydride together at elevated temperatures according to U.S. Pat. Nos. 3,306,908 and 4,239, 636. Thermal PIBSA is produced by simply heating PIB and maleic anhydride together at about 200° C. according to the procedures outlined in U.S. Pat. Nos. 3,306,908 and 4,239,636.

[2]MW designates the molecular weights of the PIB reactants determined by vapor phase osmometry (VPO).

[3]SAP designates the saponification number.

[4]Commercial TAOD is a product of BASF Wyandotte Corporation, Parsippany, NJ (BASF identifies this product as "$N_6$-amine mixture"). According to BASF's Technical Bulletin, commercial TAOD consists mainly (over 50%) of 4,8,11,15-tetra-azaoctadecane-1,18-diamine (TAOD); additional components include higher and lower homologs. The total nitrogen content is ca 28.5%, comprising 12% primary, 15% secondary and 1.7% tertiary nitrogen.

C. SYNTHESIS OF BICYCLIC AND MACROBICYCLIC POLYAMINE DISPERSANT VI IMPROVERS

Novel compositions of the instant invention having both dispersant and viscosity-index (VI) improving properties are prepared by the addition of polymers functionalized with succinic anhydride groups to the selected polyamines taught in the present invention. Virtually all polymers bearing succinic anhydride groups are responsive to the process of the present invention in generating the corresponding bicyclic and macrobicyclic polyamine derivatives. The following examples are used simply to illustrate the formation of the bicyclic and macrobicyclic polyamines using the readily available maleic anhydride grafted ethylene-propylene copolymer, i.e., ethylene propylene-succinic anhydride (EPSA) as taught in Example 1 of U.S. Pat. Nos. 4,089,794; 4,137,185; and 4,144,181.

Example C1

Synthesis of 2,6-diaza-7-Oxo-Bicyclo[4.3.0] Non-1-En-8-Yl Substituted Ethylene Propylene(EP) Copolymer Via The Aminolysis of Succinic Anhydride Substituted EP(EPSA) With 1,3,Propane Diamine (PDA).

An 11% mineral oil (Solvent 100 Neutral) solution of EP copolymer of Mn=50,000 and was grafted with maleic anhydride by heating in the presence of peroxide as shown in Example 1 of U.S. Pat. No. 4,089,794 to provide an EPSA having an acid value of about 0.14 meq. per gram of polymer.

About 200 gms of this EPSA and grafted oil was dissolved in 100 ml xylene and added dropwise to a stirred solution of 10 gms (0.135 mol) of PDA and 100 ml of xylene at room temperature. The reaction mixture was gradually heated to reflux to distill off the xylene and water of reaction. When water evolution ceased, the mixture was heated to 200° C. and sparged with nitrogen for about 2 hours. The IR spectrum of the product had a prominent C=N band at about 6 microns, which is characteristic of the bicyclic polyamine structure. Imide absorption was absent. The product analyzed for 0.34% nitrogen and had a viscosity of 2366 cSt. at 100° C. The product is represented below with n being approximately 5.

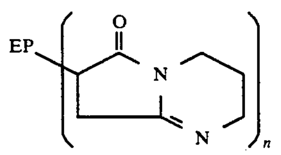

Example C2

A. The product described in Example C1 was prepared by adding the EPSA to a refluxing solution of PDA and xylene until evolution of water ceased. Analyses confirmed that the product was the same as that formed in Example C1.

B. Example C1 was repeated except that the amine used was replaced with 0.315 mole of 2-hydroxy-1,3-propanediamine. The resulting hydroxy substituted bicyclic polyamine product contained 0.38% nitrogen.

Example C3

Imidation of EPSA With 1,3-Propanediamine

This example was carried out for comparative purposes and illustrates prior art technique. A solution of 3 g PDA in 100 ml of xylene was added dropwise to 200 gms of EPSA in 100 ml of xylene stirred at 160° C. A gel formed but despite gelation, the PDA addition was completed and the reaction mixture stirred at 180° C. for 2 hours and a thickened polymer solution with an IR spectrum featuring a prominent imide absorption band. The product was too thick for viscosity measurement at 100° C. These data clearly indicate the presence of a linear chain extended product.

Example C4

Attachment of 2,6,10-Triaza-11-Oxobicyclo[8.3.0]Dodec-1-En-12-Yl Functionality Onto Ep Copolymer Via Aminolysis of EPSA With 4-Azaheptane-1,7-Diamine (AHD)

200 gms of the EPSA of Example C1 were dissolved in 100 ml xylene and added dropwise to 1.83 gm of AHD in 100 ml of xylene at room temperature. The mixture was gradually heated to reflux. The xylene and water of reaction were distilled from the reaction mixture which was then sparged with nitrogen at 180° for 1 hour. Analysis of the polymer solution by IR revealed macrobicyclic polyamine functionality (prominent absorption band at about 6 microns as depicted in the formula below. The product contained 0.5 weight percent nitrogen; n is approximately 5.

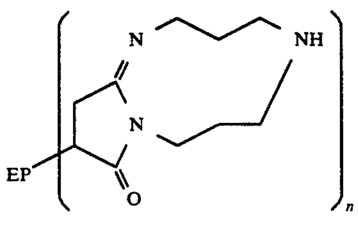

Example C5

Synthesis of 2,6,9,13-Tetraaza-14-Oxo-Bicyclo[11.3.0] Hexadec-1-En-15-Yl Substituted Ep Copolymer Via Aminolysis of EPSA With 4,7-Diaza-Decane-1,10-Diamine(DADD)

200 gms of the EPSA of Example C1 were dissolved in 200 ml xylene at a dropwise to 6 gms (34 millimoles) of DADD in 100 ml of xylene at about 25° C. under a nitrogen atmosphere. The stirred reaction mixture is heated to 180° C. and the xylene together water of reaction were gradually distilled off. The resulting polymer solution in Solvent 150 Neutral mineral oil was sparged with nitrogen and the reaction temperature was maintained at 180° C. The polymer solution featured an IR spectrum with an intense C=N absorption band, analyzed for 0.63 percent nitrogen, and had a kinematic viscosity of 365 cSt at 100° C.

Example C6

A product of Example C5 was prepared, except that the EPSA was added to a refluxing xylene solution of the polyamine. Analyses confirmed the preparation of the same product.

Example C7

This example is for comparative purposes. The same reactants were used as in Example C5, except that to a stirred solution of the EPSA in xylene at 160° C. was added dropwise 2.1 grams (0.012 mole) of DADD over an hour period. A rapid increase in viscosity was observed and the reaction mixture assumed a gel-like appearance. Heating was continued to distill off the xylene; the residue was heated to 200° C. for about 2 hours. The thickened polymer solution showed an IR spectrum with a prominent imide carbonyl absorption band at 5.95 microns, analyzed for 0.62% nitrogen and had a kinematic viscosity of 1587 cSt at 100° C.

Examples C-8 to C-12

Table 2 below contains an additional listing of dispersant—VI improvers derived from various ethylenepropylene (EP) copolymers grafter with maleic anhydride under varying conditions. The EP copolymer as 43 wt % ethylene of varying molecular weight.

TABLE 2

| Ex. | Polymer Graft Type | Polymer Mn ($\times 10^{-3}$) | Polyamine | % N |
|---|---|---|---|---|
| C8 | EP - Grafted in dichlorobenzene | 54 | PDA | 0.08 |
| C9 | EP - Grafted in polyisobutylene[a] diluent | 27 | PDA | 0.27 |
| 20 | EP - Grafted in Oil[b] | 50 | IBPA | 0.48 |
| C11 | EP - Grafted in Oil | 50 | DADD | 0.62 |
| C12 | EP - Grafted in Oil | 50 | TAOD | 0.92 |

[a]Mn = 500

[b]Oil was a Solvent 100 Neutral mineral oil

D. EXAMPLES OF DISPERSANTS PREPARED VIA AMINATION OF PIBSA WITH AZA CROWN AND AZA POLYCYCLIC COMPOUNDS.

Example D1

Aminolysis of PIBSA With 1,4,9,11-Tetra-Azacyclotetradecane(Cyclam)

6.5 gms of the PiBSA described in Example B1 and 0.5 gm (2.5 millimoles) of cyclam were combined and heated to 150° C.; the reaction mixture was stirred for several hours at 150° C. and then nitrogen sparged for two hours. The concentrate analyzed for 1.65% nitrogen, and had an IR spectrum with carbonyl absorption characteristic of an acylated cyclam product.

The above procedure was repeated except the amount of PIBSA used was doubled to reflect further acylation of the cyclam compound. The final product analyzed for 1.13% nitrogen.

Example D2

Aminolysis of PIBSA with Hexacyclen(1, 4,7,10,13,16-Hexaazacyclooctadecane).

Equimolar amounts of the aza crown compound and the PIBSA of Example B1 were combined and heated at 150° C., the mixture was stirred at this temperature for two hours and nitrogen sparged for 1 hour. The acylated hexacyclan product contained 1.5% nitrogen.

The procedure above was repeated except the amount of PIBSA was doubled. The final product contained 0.85% nitrogen.

Example D3

Aminolysis of PIBSA with 3,7,11-Trimethyl-2,6,10,13-Tetraaza-Tricyclo [7.3.1.0$^{5,13}$]Tridecane(TTT).

Approximately 115 gms (0.05 moles) of the PIBSA of Example B1 and 11.2 gms (0.05 moles) of TTT were dissolved in 100 mls xylene. The mixture was refluxed 2 hours, nitrogen sparged and filtered to give an acylated aza polycyclic product which analyzed for 1.05% nitrogen.

Example D4

Aminolysis of PIBSA With 1,4,8,11-Tetraazatricyclo-[8.4.0.0$^{4,9}$]Tetradecane (TATT).

173 gms (0.1 mole) of PIBSA of Example B8 and 19.6 gms (0.1 mole) of TATT were combined and heated at 180° for 2 hours, nitrogen sparged for 1 hour at 180° C. The acylated aza polycyclic product analyzed for 2.76% nitrogen.

E. DISPERSANT-VI IMPROVERS VIA AMINATION OF DPSA WITH AZA CROWN AND AZA POLYCYCLIC COMPOUNDS

Example E1

Modification of EPSA With 12,12-Dimethyl-2,6,10-Triazabicyclo[8.3.0] Tridec-1-En-11-One(TBT).

3.4 gms (15.2 millimoles) of TBT was dissolved in 100 ml of xylene and mixed with 55 gms of the EPSA described in Example C1; the reaction mixture was gradually heated to 150° C. for 1 hour to distill off xylene and water of reaction, then sparged with nitrogen at 160° for 1 hour. The acylated aza crown compound analyzed for 0.87% nitrogen.

Example E2

Amination of EPSA With 3,7,11-Trimethyl-2,6,10,13-Tetrazazatricyclo [7.3.1.0$^{5,13}$]Tridecane(TTT).

100 gms of EPSA of Example C1 and 3.1 gms (0.014 moles) of TTT were combined and heated at 180° for 2 hours, nitrogen sparged at 180° C. for 1 hour and cooled. The acylated azapolycyclic product analyzed for 0.43% nitrogen.

E3

Amination of EPSA With 1,4,8,11-Tetraazatri Cyclo[8.4.0.0$^{4,9}$]Tetradecane(TATT)

100 gms of the EPSA of Example C1 were mixed with 2.7 gms (13.8 millimoles) of TATT, heated to about 200° and maintained at this temperature for 2 hours with nitrogen sparging. The acylated aza polycyclic product contained 1.05% nitrogen.

Example E4

Amination of EPSA With 1,4,7,9-Tetraazatricyclo[6.3.1.0$^{4,12}$]-Dodecane (TATD).

100 gms of the EPSA of Example C1 were mixed with 2.4 gms (14.3 millimoles) of TATD and gradually heated to 200° C. The mixture was maintained at 200° C. with nitrogen sparging for 2 hours. The acylated aza polycyclic product analyzed for 1.0% nitrogen.

In Tables 3 and 4 below the products of this invention were evaluated for sludge and varnish potency in the SIB (Sludge Inhibition Bench Test) and VIB (Varnish Inhibition Bench Test). Comparative Tests with prior art products were also conducted. These tests are described below:

The SIB test employs a used crankcase mineral lubricating oil composition having an original viscosity of about 325 SUS at 37.8° C. that has been used in a taxicab that was driven generally for short trips only, thereby causing a buildup of a high concentration of sludge precursors. The oil that was used contained only a refined base mineral oil, a viscosity index improver, a pour point depressant and zinc dialkyldithiophosphate anti-wear additive. The oil contained no sludge dispersants. The quantity of such used oil was acquired by draining and refilling the taxicab crankcase at 1,000–2,000 mile intervals.

The SIB test is conducted in the following manner: The used crankcase oil is freed of sludge by centrifuging for one half hour at about 39,000 gravities (gs). The resulting clear bright red oil is then decanted from the insoluble sludge particles thereby separated out. However, the supernatant oil still contains oil-soluble sludge precursors which under the conditions employed by this test will tend to form additional oil-insoluble deposits of sludge. The sludge inhibiting properties of the additives being tested are determined by adding to portions of the used oil, a small amount of the particular additive being tested. Ten grams of each one being tested is placed in a stainless steel centrifuge tube and is heated at 137.8° C. for 16 hours at the presence of air. Following the heating, the tube containing the oil being tested is cooled and then centrifuged for 30 minutes at about 39,000 gs. Any deposits of new sludge that forms in this step are separated from the oil by decanting supernatant oil and then carefully washing the sludge deposits with 15 ml. of pentane to remove all remaining oils from the sludge. The weight of the new solid sludge that formed in test, in milligrams, is determined by drying the residue and weighing it. The results are reported as milligrams of sludge per ten grams of oil, thus measuring differences as small as one part per ten thousand. The less new sludge formed, the more effective is the additive as a dispersant. In other words, if the additive is effective, it will hold at least a portion of the new sludge that forms on heating and oxidation stably suspended in the oil so that it does not precipitate down during the centrifuging period.

In the VIB test, a test sample consisting of ten grams of lubricating oil containing the additive being evaluated is used. The test oil is a commercial lubricating oil obtained from a taxi after two thousand miles of driving with said lubricating oil. Each sample is heat soaked overnight at about 140° C. and thereafter centrifuged to remove the sludge. The supernatant fluid of each sample is subjected to heat cycling from about 150° C. to room temperature over a period of 3.5 hours at a frequency of about two cycles per minute. During the heating phase, a gas containing a mixture of 0.7 volume percent $SO_2$, 1.4 volume percent NO and the balance air was bubbled through the test samples and during the cooling phase, water vapor was bubbled through the test samples. At the end of the test period, which testing cycle can be repeated as necessary to determine the inhibiting effect of any additive, the wall surfaces of the test flasks in which the samples were contained are visually evaluated as to the varnish inhibition. The amount of varnish imposed on the walls is rated at values of from one to seven with the higher number being the greater amount of varnish. It has been found that this test correlates with the varnish results obtained as a consequence of carrying out ASTM-MS-VC engine tests.

Example G1

Evaluation of Dispersants in the SIB and VIB Tests

A series of SIB and VIB evaluations were carried out comparing macrobicyclic and polycyclic polyamine dispersants of this invention with non-cyclic linear bis-imide dispersants prepared utilizing the prior art conditions which do not provide the macrocyclic structure.

Included in the testing for comparative purposes are two dispersants CD-1 and CD-2 which are representative of current commercially available products and are made by aminating PIBSA of Mn 900 and 1300 respectively with tetraethylene pentamine to give polyisobutenyl succinimide products which are linear bis-imide structures. These results are in the table below.

TABLE

| | | EXAMPLE G1 | |
|---|---|---|---|
| ADDITIVE EXAMPLE | TYPE | SIB RESULTS MG SLUDGE/10.0 g Oil | VIB RATING |
| EX B-1 | M | 0.00 | 3 |
| EX B-4 | L | 2.93 | 5 |
| EX B-8 | M | 0.21 | 2 |
| EX B-10 | M | 0.68 | 3 |
| EX B-11 | M | 0.38 | 3 |
| EX B-12 | | 0.00 | 2 |
| EX D-4 | PC | 0.48 | 2 |
| CD-1 | L | 4.54 | 5 |
| CD-2 | L | 5.29 | 5 |

M = macrobicyclic; PC = polycyclic; L = Linear

Example G2

Evaluation of Dispersant VI Improvers in the SIB and VIB Tests.

A number of products of the invention as prepared in the foregoing examples are suitable as dispersant—VI improvers were evaluated in the SIB/VIB tests and compared for activity against a compound representative of current commercially suitable products. These results are tabulated below.

In the table, BC, MBC and PC represent the structural categorization of the products of the invention, i.e., bicyclic, macrobicyclic and polycyclic polyamine dispersant- VI improvers, respectively. CD-3 is a product which qualifies under commercial standards and is made by reaction of EPSA (Ex. C1) and N-(3-aminopropyl) morpholine, and is included for comparative purposes.

TABLE

| | | EXAMPLE G-2 | |
|---|---|---|---|
| ADDITIVE EXAMPLE | TYPE(1) | SIB RESULTS MG SLUDGE IN 10.0 g OIL | VIB RATING |
| C1 | BC | 2.04 | 1.5-2 |
| C2A | BC | 3.97 | 1.5-2 |
| C B | BC | 2.93 | 1.5-2 |
| C5 | MBC | 1.55 | 1-2 |
| C6 | MBC | 0.42 | 1.5-2 |
| C8 | BC | 4.70 | 1-2 |
| C9 | BC | 2.72 | 2-3 |
| C10 | BC | 1.36 | 2 |
| C11 | MBC | 1.75 | 1.5-2 |
| C12 | MBC | 2.51 | 1-2 |
| E2 | PC | 1.25 | 2-2.5 |
| E3 | PC | 2.37 | 2 |
| E4 | PC | 2.09 | 2 |
| CD-3 | IMIDE | 6.29 | 5 |

Example H1

Engine tests were carried out using the novel dispersant—V.I. improver multifunctional additives of this invention in the Caterpillar 1H-2 test. Lubricating oil formulations of 10W30 quality were prepared containing the novel bicyclic polyamine additive of the present invention (Example C-2A product) and these were tested in comparison with a "Base" Formulation which contained a borated polyisobutylene (Mn=980) succinic anhydride—alkylene polyamine dispersant and with a "Comparison" formulation which employed a multifunctional commercial dispersant—V.I. improver, "Acryloid 1155" which is available from Rohm & Haas Co., Philadelphia, Pa. and is a C-vinyl pyridine ethylene copolymer graft. The lubricating oils evaluated also contained, where required, conventional V.I. improver, a rust inhibitor, a metal detergent and a zinc dialkyldithiophosphate in a mineral oil base. These formulated oils were each subjected to engine testing in the "Caterpillar 1H-2" test which is an industry and government accepted test for the dispersancy and overall effectiveness of diesel oil lubricants. The results and explanation of the test are given below:

| Formulation | 240 Hour Caterpillar 1H-2 Test | |
|---|---|---|
| | TGF[2] | WTD[3] |
| Base[1] | 16.6% | 189.1 |
| Comparison | | 195 |
| Example C2A | | 119 |

[1]Base this result is an average data base for comparison in evaluating new diesel formulations and is an average of 25 engine tests.
[2]TGF top groove fill, % deposits in groove
[3]WTD weighted total demerits The Caterpillar 1H-2 test is also a U.S. Federal Test Method 791-346 and is used to meet military specifications, such as MIL-L-21260B and industry specifications, such as SAE 183 and General Motors GM 6146M. The purpose of the test is to determine the effect of an oil on ring sticking, wear and accumulation of deposits. The test uses a single cylinder Caterpillar diesel $5\frac{1}{8}\times 6\frac{1}{2}''$.

For the 1H-2 test WTD (Weighted Total Demerits) is the principal value and for a 240 hour test, the target specification is a value near the 90-100 range. This is derived from the published specification target for a 480 hour test. WTD is cumulative rating based on observation of deposits in the groove and land areas of the piston and lacquer on piston skirts with all these specific evaluations being weighted according to their relative importance and the final WTD value being calculated in accordance with the test procedure.

Example H2

A lubricating oil composition of 10W40 quality containing macrocyclic polyamine dispersant. Example B12 of the present invention together with conventional amounts of other additives to provide their normal attendant functions such as viscosity index improver, rust inhibitor, metal detergent additive, antioxidant, and zinc dialkyldithiophosphate anti-wear additives was evaluated in the ASTM VD gasoline engine test. For gasoline engine lube oils to meet the current "SF" designation of the American Petroleum Institute, lubricating oil formulations must equal or exceed certain values in the MS Sequence VD Engine Test (ASTM Special Publication 315). For dispersancy the significant values in this test are a minimum of 9.4 sludge, 6.7 piston skirt varnish and 6.6 average varnish. The Sequence VD uses a 1980 Ford 2.3 liter 4-cylinder engine and is a 192-hour test comprising the cyclic operation at varying engine speeds and temperature to simulate "stop and go" city driving and moderate turnpike operation. The test is an established industry standard. The lubricating oil of this Example gave the following outstanding results:

| | |
|---|---|
| Sludge | 9.49 |
| Piston Skirt Varnish | 8.18 |
| Average Varnish | 8.88 |

What is claimed is:

1. An oil soluble lubricating oil additive comprising a macrocyclic polyamine compound having the formula

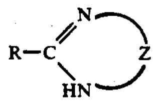

where R is a hydrocarbon having 2 to 15,000 carbon atoms and Z may be $-CH_2CH_2CH_2-$; $(CH_2CH_2CH_2NH)_nCH_2CH_2CH_2-$ where n is 1-6 or $(CH_2CH_2CH_2NH)_mCH_2CH_2(NH\text{-}CH_2CH_2CH_2)_{m'}-$ wherein m+m' is 1-5.

2. An oil-soluble lubricating oil additive comprising a macrocyclic polyamine compound having the formula:

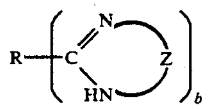

wherein R is hydrocarbon having 2 to 15,000 carbon atoms, b may be 2-150, z may be $-CH_2CH_2CH_2-$; $(CH_2CH_2CH_2NH)_n CH_2CH_2CH_2-$ wherein n is 1-6 or $(CH_2CH_2CH_2NH)_m CH_2CH_2(NH\text{-}CH_2CH_2CH_2)_{m'}-$ wherein m+m' is 1-5.

3. The oil soluble macrocyclic polyamine of claim 1 wherein R is polyisobutylene.

4. The oil soluble macrocyclic polyamine of claim 1 wherein R is an ethylene propylene copolymer terpolymer.

5. The polyamine of claim 1 where Z is $-CH_2CH_2CH_2-$ or $-CH_2CH_2CH_2(NHCH_2CH_2CH_2)_n$ where n is 1-6.

6. The oil soluble macrocyclic polyamine of claim 2 wherein R is polyisobutylene.

7. The oil soluble macrocyclic polyamine of claim 2 wherein R is an ethylene propylene copolymer terpolymer.

8. The polyamine of claim 2 where Z is $-CH_2CH_2CH_2-$ or $-CH_2CH_2CH_2(NHCH_2CH_2CH_2)_n$ where n is 1-6.

* * * * *